(12) United States Patent
Blomme

(10) Patent No.: US 8,118,860 B2
(45) Date of Patent: Feb. 21, 2012

(54) DEVICE FOR CONNECTING A TUBULAR VASCULAR PROSTHESIS TO A BLOOD VESSEL AND A VASCULAR PROSTHESIS

(76) Inventor: Adri Marinus Blomme, Groteweg (NL)

( * ) Notice: Subject to any disclaimer, the term of this patent is extended or adjusted under 35 U.S.C. 154(b) by 1228 days.

(21) Appl. No.: 11/078,325

(22) Filed: Mar. 14, 2005

(65) Prior Publication Data

US 2005/0197664 A1  Sep. 8, 2005

Related U.S. Application Data

(62) Division of application No. 09/674,258, filed as application No. PCT/NL99/00255 on Apr. 28, 1999, now Pat. No. 6,911,035.

(30) Foreign Application Priority Data

Apr. 28, 1998 (NL) .................................. 1009028

(51) Int. Cl.
*A61F 2/06* (2006.01)
(52) U.S. Cl. ...................................... 623/1.35; 623/1.36
(58) Field of Classification Search .................. 606/151, 606/153, 232, 233, 191, 192, 194, 198; 623/1.25, 623/1.35, 1.36, 1.3, 1.11, 1.14; 604/174; 600/37
See application file for complete search history.

(56) References Cited

U.S. PATENT DOCUMENTS

| | | | | |
|---|---|---|---|---|
| 4,366,819 A | * | 1/1983 | Kaster | 606/153 |
| 4,368,736 A | * | 1/1983 | Kaster | 606/153 |
| 4,592,754 A | * | 6/1986 | Gupte et al. | 623/1.25 |
| 4,657,019 A | * | 4/1987 | Walsh et al. | 606/153 |
| 5,122,154 A | * | 6/1992 | Rhodes | 623/1.13 |
| 5,330,490 A | | 7/1994 | Wilk et al. | 606/153 |
| 5,423,851 A | * | 6/1995 | Samuels | 623/1.25 |
| 5,527,355 A | * | 6/1996 | Ahn | 623/1.36 |
| 5,591,197 A | * | 1/1997 | Orth et al. | 623/1.36 |
| 5,617,878 A | * | 4/1997 | Taheri | 623/1.13 |
| 5,653,743 A | * | 8/1997 | Martin | 623/1.35 |
| 5,741,234 A | * | 4/1998 | Aboul-Hosn | 604/174 |

(Continued)

FOREIGN PATENT DOCUMENTS

| | | |
|---|---|---|
| WO | WO 93/00868 | 1/1993 |
| WO | WO 97/03616 | 2/1997 |
| WO | WO 97/39687 | 10/1997 |

OTHER PUBLICATIONS

U.S. Appl. No. 60/073,294.*

*Primary Examiner* — Brian Pellegrino
(74) *Attorney, Agent, or Firm* — Young & Thompson

(57) ABSTRACT

Suturing elements for connecting a vascular prosthesis to a blood vessel include an internal, substantially annular body intended to be received in the blood vessel in addition to an external annular body intended to lie clampingly on an outer wall of the blood vessel at least practically at the location of the internal annular body. At least one of the two annular bodies is provided with suturing members which grip in the vessel wall so as to effect an adequate fixation of at least the internal annular body. The device for use with such suturing elements and a vascular prosthesis which is provided on at least one of its outer ends with at least a part of such suturing elements are disclosed. Different embodiments of such prostheses together form a modular vascular prosthesis system. A side vessel of a thus supported blood vessel can be preserved using branch elements.

4 Claims, 8 Drawing Sheets

U.S. PATENT DOCUMENTS

| | | |
|---|---|---|
| 5,741,274 A | 4/1998 | Kinney et al. |
| 5,984,955 A * | 11/1999 | Wisselink ............... 623/1.35 |
| 5,997,573 A | 12/1999 | Quijano et al. |
| 6,004,347 A * | 12/1999 | McNamara et al. ......... 623/1.36 |
| 6,193,734 B1 * | 2/2001 | Bolduc et al. ............. 606/153 |
| 6,210,429 B1 * | 4/2001 | Vardi et al. ............... 623/1.35 |
| 6,497,710 B2 | 12/2002 | Yencho et al. ............. 606/153 |
| 6,602,281 B1 * | 8/2003 | Klein ....................... 623/1.3 |

* cited by examiner

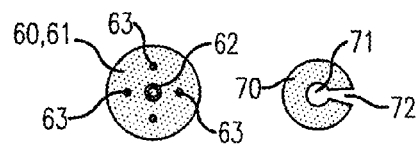
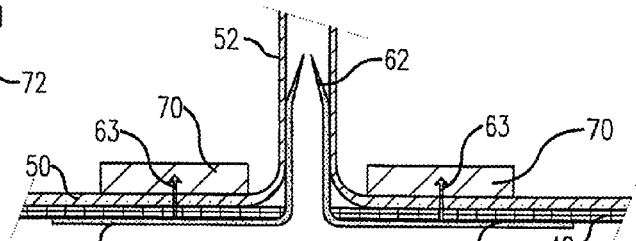
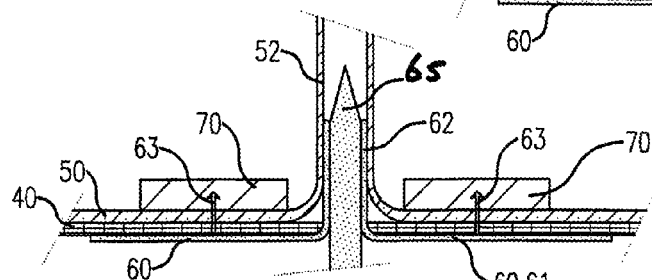
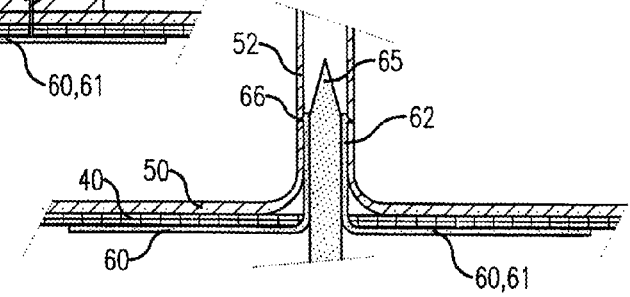
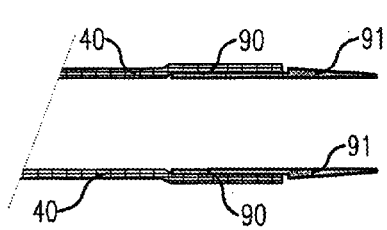
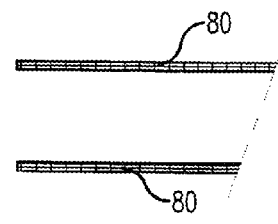
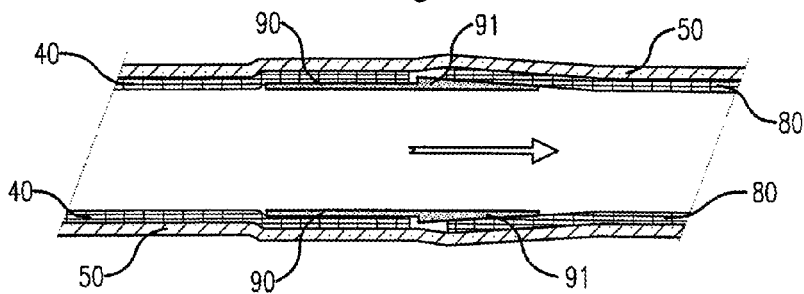

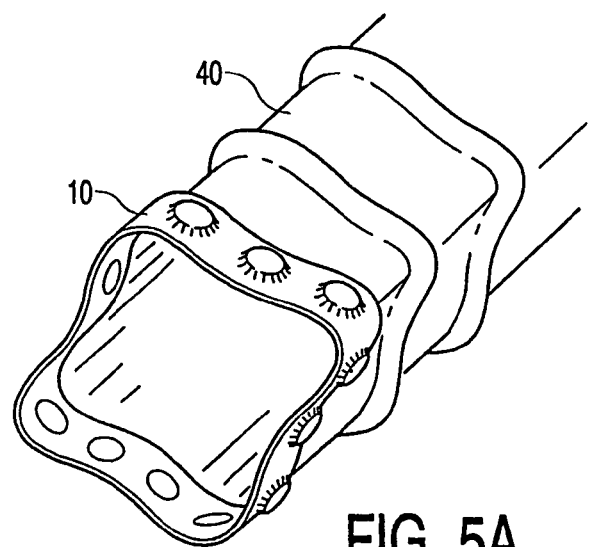
FIG. 5A
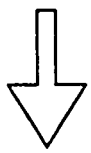
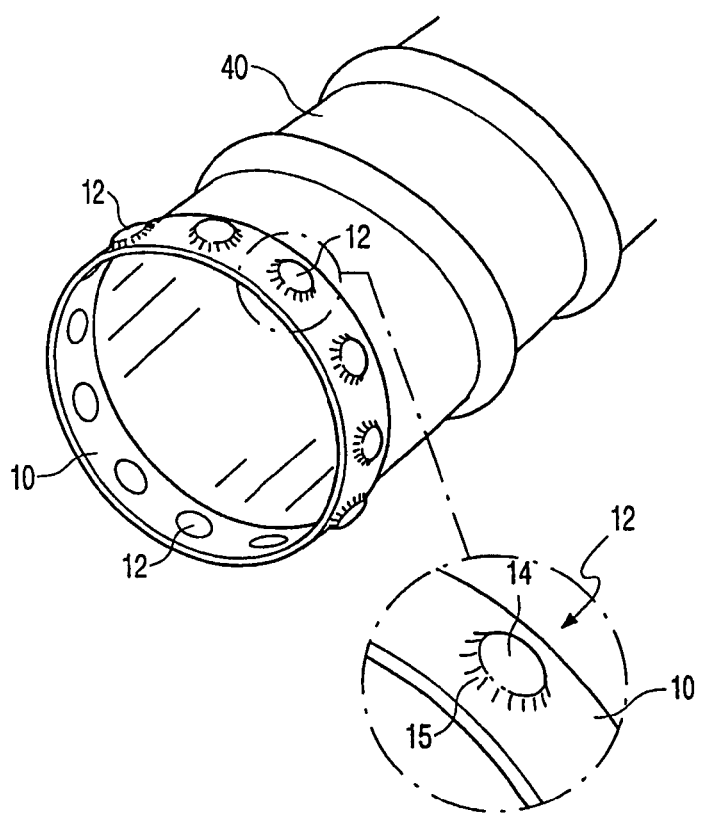
FIG. 5B

DEVICE FOR CONNECTING A TUBULAR VASCULAR PROSTHESIS TO A BLOOD VESSEL AND A VASCULAR PROSTHESIS

CROSS REFERENCE TO RELATED APPLICATIONS

This application is a division of application Ser. No. 09/674,258, filed on Feb. 2, 2001; now U.S. Pat. No. 6,911,035 which is the 35 USC 371 national stage of PCT/NL99/00255, filed on Apr. 28, 1999, which designated the United States of America. The entire contents of both of these applications are hereby incorporated by reference.

FIELD OF THE INVENTION

The present invention relates to suturing means for connecting a tubular vascular prosthesis to a blood vessel in the body.

The invention herein relates particularly, but not exclusively, to vascular prostheses intended to replace or support the natural vessel wall of particularly the aorta. Due to damage or other weakening of the wall thereof a dilation, a so-called aneurysm, can result locally herein. If timely action is not taken the vessel wall can eventually rupture at the location of such an aneurysm, resulting in internal bleeding and therewith a life-threatening situation. To avoid this the existing vessel wall is either replaced or covered with a suitable vascular prosthesis at the location of the aneurysm.

BACKGROUND OF THE INVENTION

A traditional method of arranging such a vascular prosthesis consists of opening the abdominal wall from the sternum to the pubis, whereafter an incision is made along the full length of the blood vessel at the location of the unhealthy part. A suitable vascular prosthesis in the form of a tubular body of circular knitted textile of a similar diameter and length is subsequently sutured to the healthy ends of the blood vessel with suture needle and thread. The affected vessel wall is then preferably placed round the vascular prosthesis and subsequently closed.

It will be apparent that the above specified method involves a major operation which in practice can require more than three hours. Even more important than the total duration of the operation however is that the blood flow in the vessel has to be interrupted for a relatively long time, of sometimes more than an hour. This involves a serious danger of complications both during the operation and thereafter. It will moreover be apparent that the stated size of the operation wound in this operating method also results in a relatively great discomfort for the patient and adversely affects his recovery. There is also the risk of a certain leakage through the suture, so-called false aneurysms, which may in such cases necessitate the operation being repeated.

In order to obviate these drawbacks an alternative operation technique has been developed, wherein a vascular prosthesis is arranged at the desired location endovascularly, i.e. via the vascular system itself. Such an endovascular prosthesis generally comprises a tubular body, the wall of which is formed by a metal scaffold which is resilient and capable of expanding in radial direction. The endo-prosthesis is arranged in compressed state on a tip of a catheter and manoeuvred with the catheter via a relatively small incision in the groin or another suitable place to the weakened part of the blood vessel for treating. Having arrived at the desired location, a temporary envelope is pulled off the prosthesis or a balloon incorporated in the prosthesis is expanded, whereby the prosthesis expands from the compressed to an expanded state, wherein the prosthesis lies resiliently against an inner wall of the blood vessel. Initially only the expansion force of the prosthesis holds the prosthesis in its place, but in the course of time bodily tissue will be deposited on the prosthesis whereby in the long term it will ideally be completely embedded in the wall of the blood vessel.

Such an endovascular method undeniably entails less discomfort for the patient than the classical operating method and the circulation of blood through the blood vessels also remains largely undisturbed. Nevertheless, this method also has drawbacks. Apart from the relatively high cost of this treatment there is the drawback that the suturing of the prosthesis to the blood vessel is effected initially solely by the radial spring force of the prosthesis. There is a therefore a real danger that the prosthesis can be entrained to a greater or lesser degree by the blood flow. This danger is acknowledged in an example of a known endovascular prosthesis which is described in the International patent application no. 97/39687, wherein for this purpose the proximal side of the prosthesis is provided with a ring of fine hooks to anchor the prosthesis in the vessel wall. Because it must be possible to introduce the entire unit endovascularly, the dimensions and therewith the anchoring of these hooks are inevitably limited.

There is however also the risk that the blood will be able to find its way between the wall of the blood vessel and the prosthesis and then still exert the original pressure on the vessel wall. Such a case is referred to as an endo-leak. To remedy such a complication an operation in the traditional manner will still have to be performed, whereby all advantages of an endovascular treatment method are nullified. In order to prevent this in the case of the above stated example of a known endovascular vascular prosthesis, tensioning straps are arranged at the location of both the proximal and the distal end of the vascular prosthesis, after it has been introduced, for better fixation of the whole round the vessel wall. Such a fixation is also described in the case of the endovascular vascular prosthesis known from the American U.S. Pat. No. 5,764,274. However, such tensioning straps cannot be introduced endovascularly so that a classical operation is still required for this purpose. The tensioning member of the applied tensioning straps moreover provides an undesirable irregularity in the body which may adversely affect the biocompatibility of the whole.

Finally, as a result of their necessarily fragile construction, endovascular prostheses have been found in practice to be of limited durability, whereby for the time being the quality of the prosthesis cannot be fully guaranteed in the long term.

SUMMARY OF THE INVENTION

The present invention has for its object to provide suturing means of the type stated in the preamble which allow a suturing technique which, compared to the traditional operation technique, entails only relatively minor surgery for the patient but which, compared to an endovascular method, enables a markedly more reliable suturing of the prosthesis to the vessel wall.

In order to achieve the intended objective, suturing means of the type stated in the preamble have the feature according to the invention that the suturing means comprise an internal, substantially annular body intended to be firmly connected to an outer end of the vascular prosthesis and to be received in the blood vessel, that the suturing means comprise an external annular body intended to lie clampingly on an outer wall of the blood vessel at least practically at the location of the internal annular body and that at least one of the two annular bodies is provided with suturing members which at least in connected situation thereof extend from the blood vessel substantially radially in the direction of a vessel wall and grip at least in the vessel wall so as to effect an adequate fixation of at least the internal annular body.

In order to arrange a vascular prosthesis it suffices, making use of such suturing means, to make only a small incision in or close to the affected part of the blood vessel where the vascular prosthesis will be sutured to healthy ends of the blood vessel to enable placing of the prosthesis into the vessel. Once the blood vessel has been sufficiently exposed and this incision made, the vascular prosthesis is introduced via the incision and optionally shortened to the required length. The internal annular body of the suturing means can herein already be incorporated in the prosthesis on an end thereof The vascular prosthesis is pressed sufficiently far into the blood vessel so that the end with the internal annular body of the suturing means eventually lies at the location of one of the healthy ends of the blood vessel on either side of the affected part thereof. The blood vessel is here accessible to the external annular body of the suturing means which is placed clampingly round the blood vessel at the position of the internal annular body to allow the suturing members to penetrate properly into at least the vessel wall and thus effect a reliable suturing and sealing of the prosthesis on the vessel wall. This procedure is repeated on the opposite side of the weakened vessel part with another end of the prosthesis, whereafter the vessel wall and abdomen are closed again.

It has been found in practice that the suturing means according to the invention, optionally making use of tools designed therefor such as for instance the devices which will be further described below, can be arranged within only a few seconds. The operation time, and particularly the necessary interruption of the natural blood flow through the vessel can thus be considerably limited when compared to the above specified traditional suturing method, which is of great importance particularly in the aftercare and recovery of the patient. Because at least the vessel wall is clamped between both annular bodies at the location of the suturing means, which thereby provide an effective sealing, the chance of an endo-leak is also drastically reduced, if not completely eliminated, by the suturing means according to the invention. Furthermore, the prosthesis is adequately fixed to the vessel wall by means of the internal annular body, whereby the danger of undesired shifting of the prosthesis in the blood vessel is likewise prevented, or at least greatly reduced. Because the annular body and the vascular prosthesis are introduced by classical means, no concessions have to made in their material and construction as in the case of an endovascular insertion technique. The internal annular body can therefore be relatively robust so as to be able to sufficiently counterbalance the forces exerted radially thereon by the external annular body and thus ensure an adequate fixation of the vascular prosthesis. For the prosthesis itself a traditional tubular body can be used per se, the long term durability thereof having by now been sufficiently tested, this in contrast to tubular bodies provided with stents, whether or not self-expanding, applied in endovascular treatment methods. The invention nevertheless requires only a small incision and the operating time, and more particularly the period of time for which the bloodstream is blocked, is considerably shorter than in the fully classical treatment method, which radically reduces the risk of mortality and other complications. The invention thus combines the advantages of both the known methods described above, i.e. relatively rapid and minimal surgery together with a reliable fixation and sealing of the prosthesis on the vessel wall, without the associated drawbacks.

In a particular embodiment the suturing means according to the invention are characterized in that the suturing members, at least in the connected situation, extend radially from a first of the two annular bodies and are received in the other of the two annular bodies to thus effect a firm mutual connection while enclosing the wall of the vascular prosthesis and the vessel wall. In this embodiment the vessel wall and the vascular prosthesis are as it were clamped between both parts of the suturing means, wherein the suturing members provide a through mutual anchoring of the diverse parts. An exceptionally reliable suturing is thus obtained, which owing to the invention can be arranged in an extremely short time.

In a further embodiment the suturing means according to the invention are characterized in that the first annular body comprises a metal ring with lips which can be pressed radially outward and are provided with sharp protrusions which are capable of penetrating through the wall of the prosthesis, the wall of the blood vessel and into the material of the other of the two annular bodies. After the first annular body has been brought into position, the lips are pressed out with or without the use of a special accessory so that the sharp protrusions penetrate into the other annular body. The protrusions are herein preferably provided with one or more barbed hooks to ensure their fixation in the material of the other annular body.

A preferred embodiment of the suturing means according to the invention has the feature that the suturing members extend from the internal annular body and that the external annular body comprises at least a core of plastic for receiving the suturing members therein. Because the suturing members herein extend from the internal annular body and pass through the vessel wall to the outside to be received in the other annular body, the internal annular body can be relatively thin, whereby the natural blood flow is thereby disturbed as little as possible. In this respect an inner diameter is preferably chosen for the internal annular body which is equal to that of the original blood vessel and the blood vessel is slightly stretched to allow nesting of the annular body therein so that no turbulences or other disturbances whatsoever are caused in the blood flow. A visual inspection is thus further possible to establish that the normally sharp ends of the suturing member are actually lying in the other annular body and not outside it. Preferably applied herein is a tough or foamed plastic which allows for a relatively easy penetration of the suturing members and then firmly fixes the suturing members.

To enable a simple positioning of the external annular body round the blood vessel, a further particular embodiment of the suturing means according to the invention has the feature that the external annular body comprises a ring which is interrupted in at least one position and that at the location of the interruption closing means are provided to mutually connect adjacent ring parts. The blood vessel is herein inserted in the opened ring, whereafter the ring is closed using the closing means. The closing means for instance comprise a suturing member which extends from one of the two ends of the annular body and is capable of penetrating in fixing manner into the material of the other end. More particularly the closing means are adjustable so that the external body can be clamped and closed tightly round the internal one.

In a preferred embodiment the suturing means according to the invention have the feature that the external annular body comprises at least on a side facing the blood vessel a regular pattern of cams with which the body supports on the blood vessel, which cams leave mutually free interspaces extending over the full width of the body. Because in this embodiment at least one of the two annular bodies does not support on the blood vessel wall along its full surface but only with a regular pattern of cams between which channels remain clear, the blood vessel wall is prevented from being completely clamped off by the suturing means whereby the blood circulation therethrough could be endangered and the blood vessel wall could die off. The channels formed by the continuous interspaces effectively prevent this.

The prosthesis, preferably already provided with the internal annular body, is inserted into the blood vessel with a suitable tool. For adequate fixing herein of the internal annular body located inside the prosthesis a further particular embodiment of the suturing means according to the invention has the feature that the means also comprise a clamping ring which is intended to lie against an outer wall of the prosthesis at least practically at the position of the internal annular body and herein exert at least locally a radially inward directed force. More particularly the clamping ring herein comprises a crimp ring which can permanently decrease in diameter at increased temperature. After specified heating such a ring crimps around the prosthesis having therein the internal annular body of the suturing means, so that the prosthesis is clamped between the two. This ensures an adequate fixation of the internal body in the prosthesis.

In a further particular embodiment the suturing means according to the invention have the feature that the suturing members comprise protrusions which extend from the internal annular body on a side thereof directed toward the blood vessel wall and are capable, at least under the influence of a radially directed force, of penetrating at least partially the blood vessel wall to thus anchor the prosthesis therein. More particularly the suturing members herein comprise a regular pattern of crater-like openings, the walls of which form the protrusions. It is not necessary herein for the suturing members to penetrate completely through the vessel wall in order to penetrate for instance into an external annular body. An adequate gripping in the vessel wall will already suffice. This embodiment is herein based on the insight that in the bloodstream mainly axial forces will be exerted on the suture and not much in the way of radial forces, whereby an axial anchoring such as by means of the suturing members referred to here is in itself sufficient. The external annular body is able to provide the counterpressure possibly required herein at the moment the suturing members penetrate into the vessel wall. Furthermore, the external body will in this case also prevent the occurrence of possible endo-leaks, now that it can be placed tightly round the internal body while enclosing at least the vessel wall.

A further particular embodiment of the suturing means herein has the further feature according to the invention that the internal annular body has an inner diameter which is at least practically equal to an outer diameter of the vascular prosthesis and that the internal annular body is intended to lie against an outer wall of the vascular prosthesis. The internal annular body can be fixed by means of a suitable glue or otherwise on the outer wall of the vascular prosthesis, so that the protrusions do not have to be pressed through the prosthesis wall and can thereby be shorter. This reduces the chance of damage to the inner wall of the blood vessel during an operation, wherein a prosthesis provided with such an annular body is guided to the desired location via the blood vessel.

To further reduce this risk and also to enable insertion of the whole in simple manner in a blood vessel, a further embodiment has the feature herein that the internal annular body comprises a deformable ring which in a first contracted state has a diameter which falls within the diameter of the blood vessel and in a second expanded state is able to lie against an inner wall of the blood vessel. In the first contracted state the deformable ring, lying round the vascular prosthesis, can be inserted without difficulty into the blood vessel and manoeuvred to the desired position. There the ring is expanded to the full diameter so that the ring eventually lies against the vessel wall and the suturing members penetrate therein. This can be realized in a very short time and in particularly reliable manner making use of a special tool such as the device to be further described hereinbelow, so that here also the unavoidable disruption of the natural blood circulation during the operation is limited.

In a conventional operating method side vessels of a blood vessel are usually lost at the location of a vascular prosthesis arranged therein because such side vessels are closed off by the vascular prosthesis. The invention also provides, on the basis of the same principle as the above specified suturing means, branch means for connecting a side vessel of a main blood vessel to a vascular prosthesis arranged in the main blood vessel, which branch means make it possible to preserve a possible side vessel. According to the invention such branch means comprise a flange-shaped internal body intended to lie against an inner wall of the vascular prosthesis, which flange-shaped body carries on its side directed toward the vascular prosthesis a hollow stem open on both sides as well as at least one suturing member, both of which are able to penetrate through the wall of the vascular prosthesis, and comprise a flange-shaped external body intended to lie round the side vessel against an outer wall of the main blood vessel at the position of the internal body, which external body is provided with a bore for receiving the side vessel and the stem therein, wherein at least in mutually connected state the suturing member is received in the external flange-shaped body, thus forming a firm mutual connection, and the stem is received in the side vessel, thus forming an open connection between the main blood vessel and the side vessel. The internal body is herein pressed through the prosthesis wall as a kind of thumbtack with the stem and the at least one suturing member, wherein the stem is carried into the side vessel. The at least one suturing member penetrates adjacently of the side vessel through not only the prosthesis but also the vessel wall. The external body is placed round the side vessel and pressed firmly together with the internal body so that the suturing member penetrates in the material of the external body and thus effects a firm connection. In this manner the hollow stem provides an open communication between the prosthesis in the main blood vessel and the side vessel, which latter is thus preserved.

In a preferred embodiment of the branch means the stem tapers to a point at its free end in order to facilitate penetration thereof through the prosthesis wall. Although for the mutual connection of the two flange-shaped bodies a single suturing member will optionally suffice, a preferred embodiment of the branch means has the feature that the internal body comprises at least two suturing members which are disposed around the stem. For the purpose of simple positioning of the external body a further preferred embodiment of the branch means according to the invention has the feature that the external disc-like body comprises a channel which provides access to the bore from a peripheral edge. The side vessel can herein be inserted in the bore in simple manner via the channel.

The invention also relates to a device for inserting and suturing a flexible tubular vascular prosthesis in the body, which prosthesis is provided on a free end with an annular body which lies against a wall thereof, comprising a flexible infeed line, which infeed line is provided on one end with a fixation member intended for receiving thereon the vascular prosthesis with the internal annular body, which fixation member is able when energized to exert a radially outward directed force on the annular element.

The prosthesis is pushed into the affected blood vessel making use of such a device using the flexible infeed line, wherein the fixation member holds the prosthesis precisely in place. At the intended location the fixation member is energized to thus press the prosthesis with the annular body radially outward. The prosthesis with the annular element is thus pressed from the inside against the vessel wall, which herein preferably receives a counterpressure from outside in the form of a second annular body forming part of the suturing means according to the invention and arranged round the blood vessel at that position. Owing to the action of said force the suturing members provided on at least one of the two annular bodies will be able to adequately penetrate at least the vessel wall and thus achieve a reliable fixation of the vascular prosthesis.

In a particular embodiment the device according to the invention has the feature that the annular body comprises a metal ring with suturing members which can be pressed radially outward and that the fixation member is able to exert a radially outward directed force on at least the suturing members of the annular body. In this embodiment the radial force is not so much exerted on the annular body as a whole but more specifically on the outward pressable suturing members which thereby penetrate into or even through the vessel wall.

A further particular embodiment has the feature herein that the suturing members comprise lips with sharp ends which are retracted and can be pressed radially outward and that the fixation member comprises a rotatable disc for receiving the annular body thereon, which disc is provided with recesses for receiving the lips of the annular body therein. In this embodiment the suturing members are formed by outward pressable lips which are initially directed inward and therefore lie at least partially retracted in the ring. The retracted lips herein fall into the recesses of the disc and will be forced radially outward when the disc is rotated and the lips are herein driven out of the recesses. Such a retracted positioning facilitates insertion of the prosthesis provided with the annular body and prevents unintentional damage to the vessel wall during transport to the suturing location. At the intended location the lips are forced out of the respective recesses by appropriate rotation of the disc. All lips will thus penetrate with their sharp end at least almost simultaneously at least into the vessel wall to effect the desired suturing.

In order to prevent the annular body co-rotating under the influence of the rotation of the disc, a further particular embodiment of the device according to the invention has the feature that the fixation member comprises two discs which are rotatable in opposing directions and are mutually adjacent and which together receive the annular body thereon, which discs are both provided with recesses for receiving therein lips of the annular body which are retracted in opposing directions and which can be pressed radially outward. By thus performing two rotations in opposing directions in the fixation member which act upon the internal annular body, at least practically no net force is exerted thereon so that possible co-rotation of the annular body is prevented. This is particularly important if the suturing members of the annular body have to be received at a precisely determined location in for instance a second annular body which has been arranged externally round the vessel wall.

In a further particular embodiment the device according to the invention has the feature that the fixation member comprises an inflatable body which in a first at least partially evacuated state can be received in the prosthesis with the annular body and in a second filled state takes on a cylindrical form coaxially with the prosthesis, an external diameter of which is at least practically equal to an internal diameter of the vascular prosthesis. Such a fixation member has a relatively simple mechanical construction and is found in practice to have sufficient expansion force to press the vascular prosthesis with the annular body sufficiently firmly from the inside against the vessel wall to thus enable suturing members to at least penetrate adequately therein.

In order to avoid overloading of the vessel wall herein and retain full control over the expansion behaviour of the inflatable body, a preferred embodiment thereof has the feature according to the invention that in the second state the inflatable body is at least practically non-stretch and herein maintains an internal pressure in the order of magnitude of several tens of atmospheres. In inflated form such a fixation member behaves as a rigid and practically non-compressible body which is thereby highly suitable for absorbing and compensating possible counterpressure on the suturing members. In evacuated state such a fixation member is in contrast flexible and yielding, whereby together with or without a prosthesis arranged thereon it allows of exceptionally easy manoeuvring via the blood vessel to the desired location.

A further embodiment of the device according to the invention has the feature that the device comprises a second fixation member intended for fixing a second annular body, which second annular body is intended for lying against an outer wall of a blood vessel and that monitoring means are provided for indicating the mutual position of both fixation members. The second annular body is placed round the blood vessel with the second fixation member at a location which corresponds precisely with that of the first internally arranged annular body on the first fixation member. To enable adequate control of this relative position, the monitoring means provide an accurate indication of the mutual position of both fixation members and therewith of both annular bodies. A precise alignment of the respective positions of both annular bodies can thus be realized in simple manner. The suturing members of at least one of the two bodies can subsequently be driven into at least the vessel wall to thus ensure an adequate enclosing and anchoring of the vascular prosthesis on the vessel wall.

The invention further relates to a vascular prosthesis comprising a flexible tubular body intended to be connected to a blood vessel with a first and a second end respectively at a first and a second location.

In order to enable such a vascular prosthesis making use of the suturing members and device according to the invention to be arranged in the body of a patient in a short time, such a vascular prosthesis according to the invention has the feature that the tubular body comprises an opening in a wall thereof between the first and second end. This opening provides a passage for the suturing means and device according to the invention for realizing therewith said connections at the first and second location. After the first end of the prosthesis has been sutured, the second or further end of the prosthesis can be fixed in similar manner from the inside via the opening in the prosthesis. Following this operation the opening in the prosthesis is closed and the vessel wall sutured at this location, whereafter the bloodstream can resume its natural flow. To facilitate closing of the prosthesis a preferred embodiment thereof has the feature according to the invention that the tubular body comprises an externally directed collar around the opening. In such an embodiment only the collar has to be closed to close the prosthesis adequately. For this purpose a lace can for instance be provided in the collar with which the collar can be laced up, although such a collar can also be closed extremely quickly in other manner, such as for instance by means of stapling.

A further vascular prosthesis comprising a flexible tubular body, at least a first end of which is intended for connecting to a blood vessel has the feature according to the invention that the tubular body is provided on at least the first end with an internal annular body of the suturing means according to the invention. A first particular embodiment of such a prosthesis according to the invention, wherein the internal annular body lies against an inner wall of the tubular body, has the feature herein that a clamping ring lies clampingly on an outer wall of the tubular body at the location of the internal annular body. A second particular embodiment of such a prosthesis according to the invention has the feature herein that the internal annular body lies on an outer wall of the tubular body via a suitable glue connection. Such prostheses are ready for immediate use at least on the relevant end and can be supplied including the relevant parts of the suturing means in a sterilized packaging, which saves (preparation) time during the operation.

A further preferred embodiment of the vascular prosthesis according to the invention has the feature that a second end of the tubular body is provided with coupling means which are capable of a liquid-tight coupling to a free end of a second flexible tubular body. More particularly this preferred embodiment according to the invention is characterized in that the coupling means comprise a rigid, tubular coupling element which is firmly connected on a first side to the second end of the tubular body and comprises on a second part a taper intended for clampingly receiving thereon the free end of the second tubular body. A rapid coupling can thus be established extremely rapidly between both tubular bodies wherein the free end of the second tubular body simply has to be pushed onto the taper. In order to secure this connection a further particular embodiment of the vascular prosthesis according to the invention is characterized in that the coupling element is provided at the location of the taper with at least one external, tangentially running rib which extends over at least a part of the periphery of the taper and more particularly in that the coupling element comprises at the location of the taper at least two external ribs which leave a certain mutual interspace, which interspace is intended for receiving a clamping ring at that position which fixedly clamps the end of the second tubular body onto the taper. The free end of the second tubular body is pushed over this rib or ribs onto the taper, whereafter the rib and optionally the clamping ring keeps the second tubular body from sliding off unintentionally.

A prosthesis provided with such coupling means can be sutured on the first end to a healthy end of the blood vessel in the above described manner, while the second end provides the option of a liquid-tight rapid coupling to another, possibly similar vascular prosthesis. It is hereby unnecessary to perform a second or further suturing from the inside of one and the same prosthesis, and the sutures can be placed independently of each other and the different free ends can be mutually connected by means of the coupling means described here. Not only can additional time be gained in practice due to such a rapid coupling, but the possibility is also provided of a modular construction of a vascular prosthesis system of mutually connectable prosthesis elements, to which prosthesis system the invention therefore also relates. In addition to single prosthesis elements with only a main leg which is arranged on either side between healthy ends of the affected blood vessel, this vascular prosthesis system for instance also comprises more complex elements which are adapted in respect of design to specific surgery.

A particular embodiment of the vascular prosthesis according to the invention provides as such a module which is specifically suitable for realizing a so-called end-to-side anastomosis. This particular embodiment of the vascular prosthesis has the feature that the tubular body comprises a main leg, between opposite ends of which at least one side leg extends, and that at least one of the free ends of the tubular body carries either an internal annular body associated with the suturing means according to the invention or coupling means of the above specified type. More particularly this embodiment has the feature that the main leg is provided on either side with such an internal annular body. In this embodiment the main leg can be fully inserted into a healthy blood vessel and fixedly sutured therein on either side in the above described manner. The at least one side leg of the prosthesis then provides a branch of this blood vessel and can be sutured, either directly or via the above specified coupling means and a further vascular prosthesis, to an end of a further blood vessel, thus realizing an end-to-side anastomosis.

Another particular embodiment of the vascular prosthesis according to the invention is characterized in that the tubular body comprises a primary leg with a first free end and a second end which divides into at least two secondary legs and that at least one of the free ends of the tubular body carries either an internal annular body associated with the suturing means according to the invention or coupling means of the above specified type. This embodiment is eminently suitable and thereby provides appropriate modular elements of the prosthesis system according to the invention for the purpose of a so-called end-to-end anastomosis, particularly one close to the bifurcation, wherein a healthy end of a blood vessel must be connected to usually two other healthy ends of blood vessels.

For the complete replacement or support of a bifurcation of the chest or stomach aorta, a particularly practical embodiment of the vascular prosthesis herein has in this respect the feature according to the invention that the primary leg is provided on the first end with an internal annular body and that the secondary legs each carry coupling means on their free end. The primary leg is herein sutured to a healthy end of the aorta, while the secondary legs are coupled to healthy ends of the arteries branching therefrom via single prostheses which can each be individually shortened to the desired length.

Suitable for a more general end-to-end anastomosis and smaller bifurcations is a further particular embodiment of the vascular prosthesis according to the invention which is characterized in that at least the secondary legs are each provided at their free end with an internal annular body. These secondary legs can be sutured according to the invention directly to the branches of a blood vessel which is itself coupled to the primary leg either directly or via a further vascular prosthesis according to the invention.

BRIEF DESCRIPTION OF THE DRAWINGS

The invention will now be further elucidated and explained on the basis of a number of embodiments and an associated drawing which further illustrate the invention but do not in any way limit the invention in its range and scope. In the drawing:

FIGS. 4A-4C show different cross-sections of an embodiment of branch means according to the invention;

FIGS. 5A-5B show in perspective view a second embodiment of suturing means and a vascular prosthesis according to the invention;

FIGS. 8A-8B show a detail drawing in cross-section of a rapid coupling with an embodiment of the vascular prosthesis according to the invention.

DETAILED DESCRIPTION OF THE INVENTION

Figure 1A:
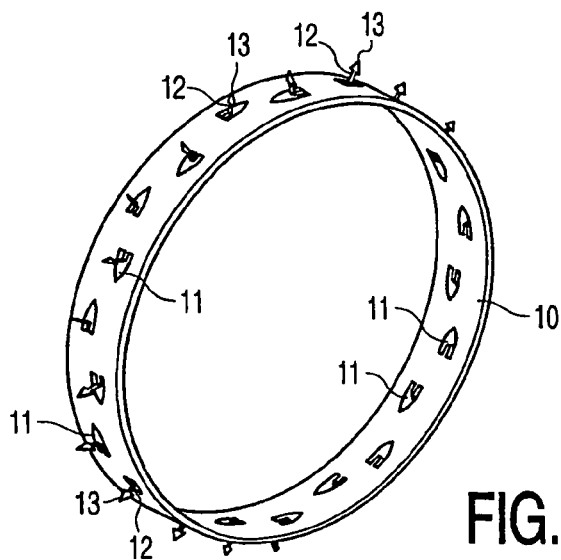
FIGS. 1A-1C show a perspective view of a first embodiment of the suturing means according to the invention.

The figures are purely schematic and not drawn to scale. Some dimensions in particular are (highly) exaggerated for the sake of clarity. Corresponding components are designated as far as possible in the figures with the same reference numerals.

Figure 1B:
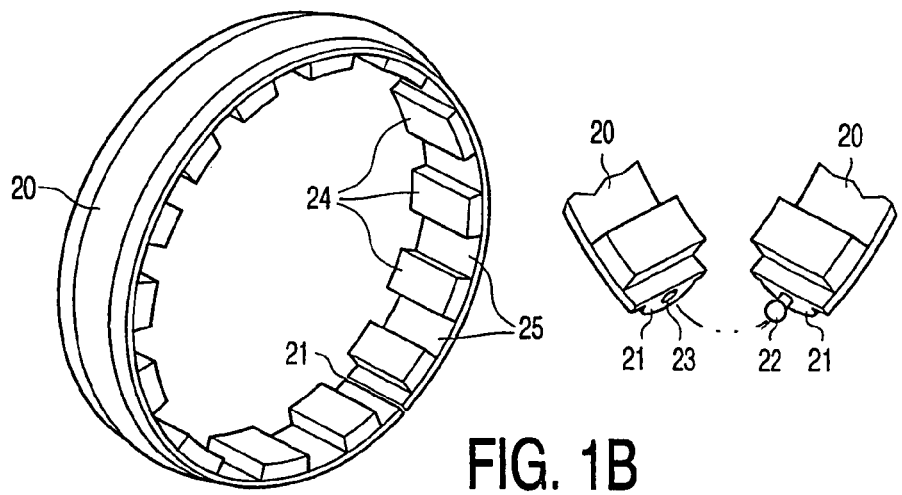

The suturing means of FIGS. 1A-1B comprise an internal annular body 10, see FIG. 1A, in the form of a closed ring of high-grade steel or another biocompatible metal or metal alloy. Arranged in the wall of the ring at regular positions are notches 11 which provide space for suturing members 12. The suturing members here comprise a regular pattern of lips 12 with sharp protrusions 13. The lips are initially retracted radially but in the shown situation are pressed radially outward, in which case lips 12 are able to penetrate through the vascular prosthesis and the vessel wall, which will be further elucidated hereinbelow.

The suturing means further comprise an external annular body 20, see FIG. 1B, in the form of a ring with at least a core of plastic. In this embodiment the ring is wholly manufactured from a plastic and with a sufficient thickness such that ring 20 can receive suturing members 12 therein in clamping and snapping manner, so that a reliable gripping and mutual connection is effected. Other than the internal body, external ring 20 does not comprise an integral unit but ring 20 has an interruption 21 where closing means are provided to hold together adjacent ring parts. The closing means here comprise a snap member 22 which snaps precisely into a complementary bore 23 in the adjacent ring part, this being shown in more detail in the indicated circle. If desired, more of such snap members can be provided so that ring 20 is adjustable and can be adapted to the actual dimensions of the blood vessel. Ring 20 can thus be opened and closed manually. Ring 20 comprises on its inner side a regular pattern of cams 24, whereby ring 20 is able to support on an outer wall of a blood vessel while leaving clear interspaces 25. The interspaces 25 extend over the full width of ring 20 and thus provide continuous channels which ensure sufficient blood circulation through the vessel wall to prevent undesired dying off thereof.

Figure 1C:
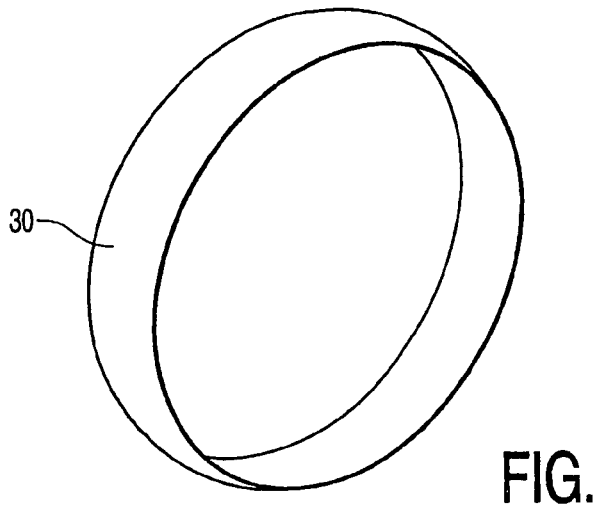

The suturing means of this embodiment further comprise a clamping ring 30, see FIG. 1C. The clamping ring here comprises a crimp ring manufactured from a suitable crimp foil of plastic and is therefore no more than an extremely thin band which is nevertheless capable of exerting a substantial radially inward directed force when it is permanently reduced in diameter at increased temperature.

In order to suture a vascular prosthesis to a blood vessel in the body making use of such suturing means, an incision is made therein at the position of or close to the affected part to be replaced or supported after the blood vessel has been exposed over a sufficient length, wherein a length of no more than a few centimetres usually suffices. Via this incision the vascular prosthesis is inserted into the blood vessel, for instance using the embodiment of the device according to the invention shown in FIG. 2.

Figure 2:
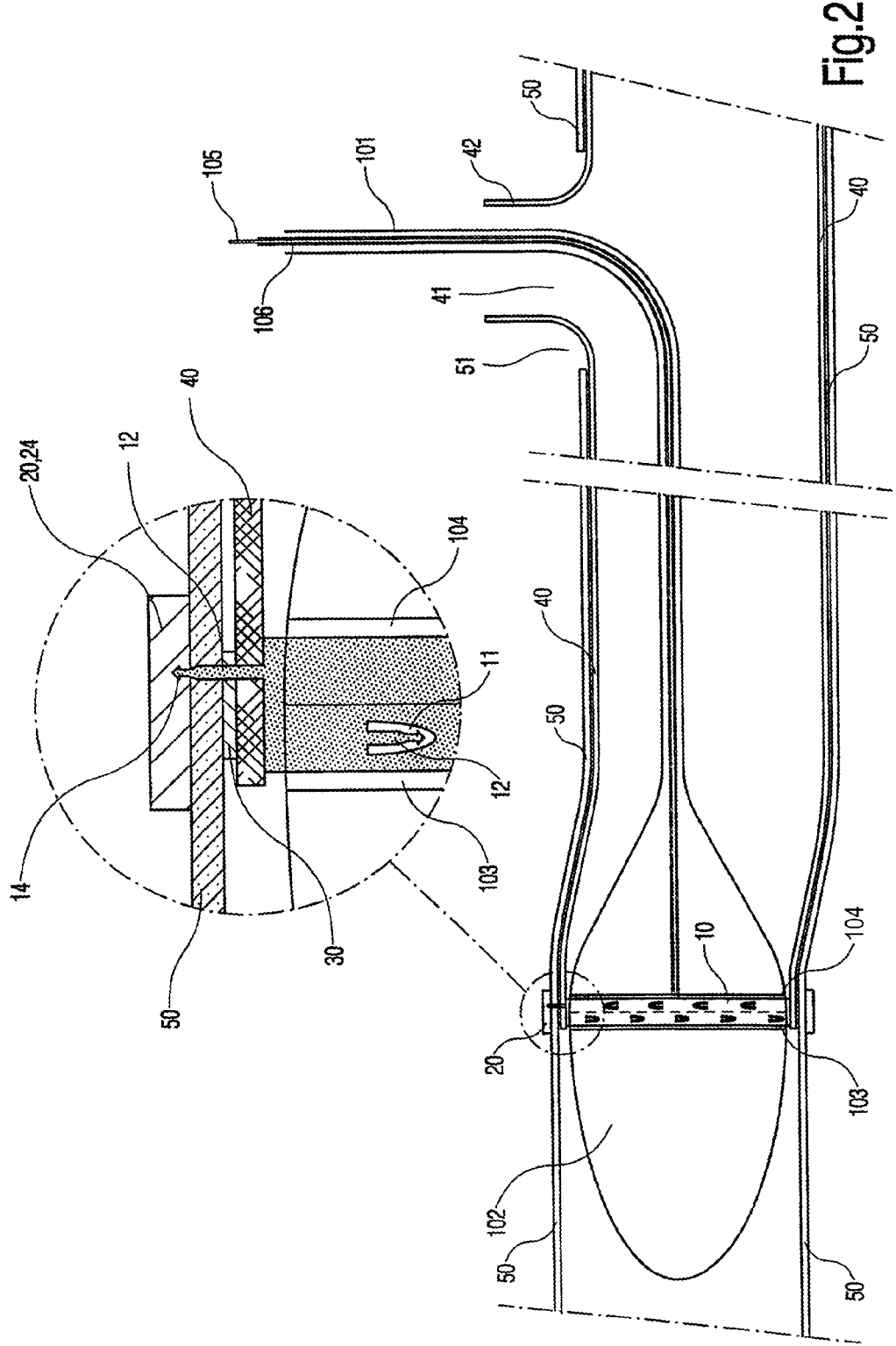
FIG. 2 shows a longitudinal section of a first embodiment of the device and a vascular prosthesis according to the invention.
Figure 3A:
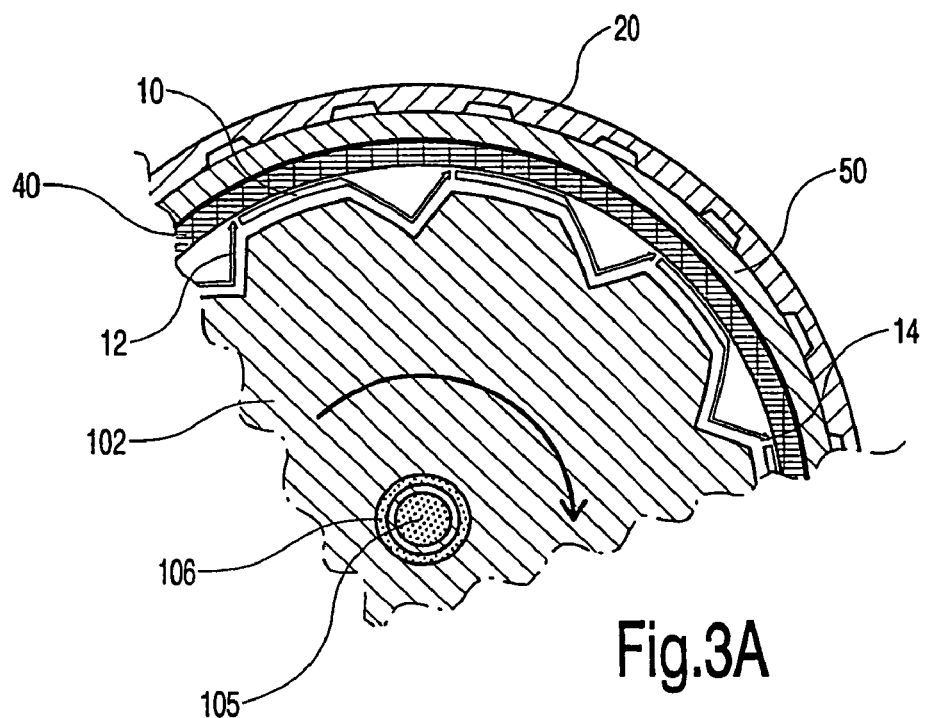
FIGS. 3A-3B show two cross-sections of the device of FIG. 2 in successive stages of operation.
Figure 3B:
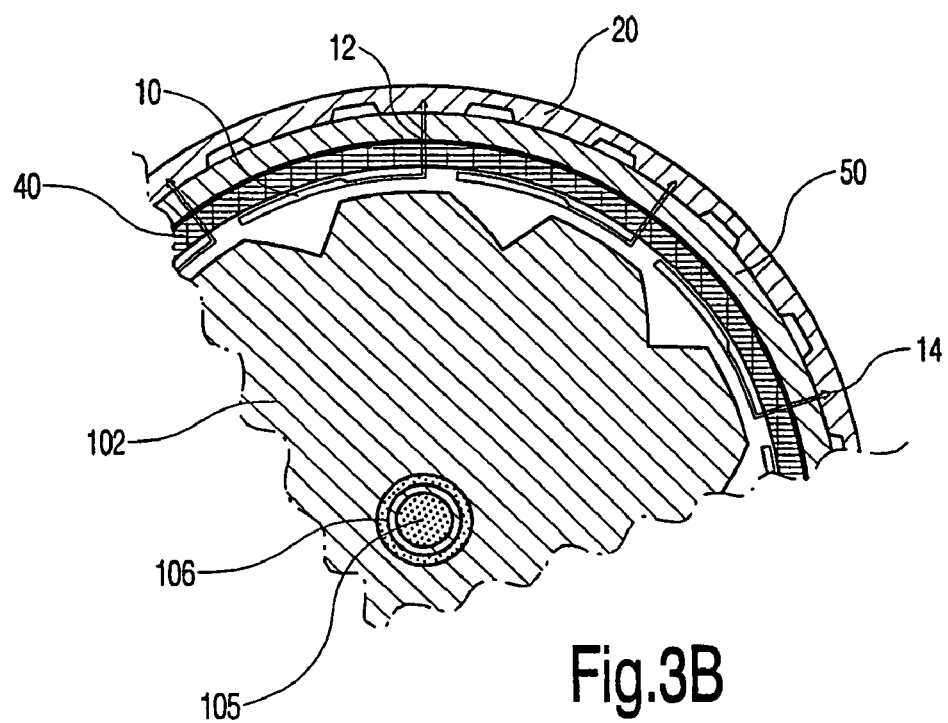

The device shown in FIG. 2 comprises a hollow, flexible infeed line 101 which is provided at one end with a fixation member 102 which is intended for receiving the vascular prosthesis thereon. Vascular prosthesis 40 is herein provided on a free end with the above described internal annular body 10 which lies against an inner wall of prosthesis 40. The above specified crimp ring 30 holds prosthesis 40 and internal ring 10 firmly together. The retracted suturing members 12 of internal ring 10 fall into corresponding recesses in a rotatable disc 103,104 forming part of fixation member 10, see also FIGS. 3A and 3B. In this embodiment the fixation member comprises two such discs 103,104 which rotate in mutually opposing directions, driven herein by separate drive shafts 105 respectively 106 which are guided thereto via the hollow infeed line. Owing to this retracted position of the suturing members the whole of prosthesis 40, inner ring 10 and crimp ring 30 are properly fixed on fixation member 102.

Lying on fixation member 102 the prosthesis 40 is guided with infeed line 101 into the weakened or at least affected blood vessel 50 via a relatively small incision 51 arranged herein which must be just large enough to enable passage of fixation member 102. At the intended location the above specified external annular body 20 is placed round blood vessel 50. The device can optionally be provided herein with a second fixation member to thereby fix this external annular body 20 onto vessel wall 50, wherein monitoring means are moreover optionally provided which indicate the mutual position of both fixation members so as thus to be certain that both annular bodies 10,20 lie opposite one another in sufficiently precise manner.

In this situation both discs 103,104 in the first fixation member are rotated a small turn in opposite directions from outside using shafts 105,106 so that the initially retracted suturing members 12 of the internal ring are driven out of the recesses of the discs. The radially outward directed force exerted therein on internal ring 10, or at least on suturing members 12 thereof, ensures that suturing members 12 are raised and penetrate through prosthesis 40, crimp ring 30 and vessel wall 50 and are thus received in the material of external ring 20, see also FIGS. 3A and 3B which show the situation respectively before and after this rotation. Barbed hooks 14 on sharp ends 13 of the suturing members herein ensure an effective connection practically free of play to outer ring 20. Each of the suturing members 12 on inner ring 10 thus penetrates at the same moment into outer ring 20 whereby an extremely reliable connection is established to the outer ring. The rotation is preferably performed by means of a pistol-like mechanism on the end of drive shafts 105,106 whereby the rotation, and therewith the suturing of the vascular prosthesis, can be performed extremely accurately in a fraction of a second. The opposing rotation direction of the two discs herein ensures that at least practically no net tangential force is exerted on the internal ring and the vascular prosthesis, so that these remain accurately in place.

Once the operation has been thus performed on this side of the vascular prosthesis, it is repeated on the opposite side. In order herein to provide passage to infeed line 101 with fixation member 102 the vascular prosthesis is itself also provided according to the invention with an opening 41 between both ends. As soon as the second suture has also been made in similar manner, fixation member 102 is removed and this opening 41 in vascular prosthesis 40 is closed. So as to simplify this, the vascular prosthesis according to the invention comprises an externally directed collar 42 which can be simply closed by stapling or closed in a short time using a lace or the like. Finally, the incision 51 made in the vessel wall is sutured, whereafter the bloodstream can resume its natural flow. The patient is now ready for further post-treatment, wherein inter alia the skin is closed, and subsequent recovery from the operation. As a result of the invention the entire operation all in all requires markedly less time than a more conventional operating technique wherein a suture is placed manually to stitch the prosthesis and the blood vessel together, wherein particularly the necessary interruption of the blood flow can be considerably shorter owing to the invention. The clamping enclosure of vessel wall 50 between internal ring 10 and external ring 20 moreover reduces the chance of so-called false aneurysms or endo-leaks which in some cases of said conventional surgical respectively endovascular operating techniques may afterward completely negate the result of the operation.

In a conventional operation technique small side vessels of the blood vessel will normally be closed off by the prosthesis whereby the circulation to the organs supplied thereby will be obstructed and these organs can become inactive in the course of time or can even die off. The invention does however provide a possibility of preserving the circulation via such side vessels in the form of branch means based on the same suturing principles as the above specified suturing means. A number of embodiments thereof is shown in FIGS. 4A-4D.

The branch means drawn in FIG. 4A comprise a flange-shaped internal body 60, see FIG. 4C, which is intended for lying against an inner wall of main blood vessel 50, as shown in FIG. 4A. Body 60 is manufactured from a high-grade biocompatible material, for instance a high-grade form-retaining plastic, steel or other metal or metal alloy, and can optionally be embodied slightly curved to allow flange 61 to connect better onto the radius of blood vessel 50. On one of its two sides the body 60 carries a hollow stem 62 open at both ends which is able to penetrate through prosthesis 40. Stem 62 in this case tapers slightly on its outer end and thus forms a mandrel facilitating various aspects. Four suturing members 63 stand on the flange around mandrel 62.

The branch means further comprise an external flange-shaped external body 70, see also FIG. 4C, which lies on the outside of main blood vessel 50 against the vessel wall thereof. External body 70 is manufactured from a plastic which allows a penetration of suturing members 63 therein. The external body comprise a through-bore 71, in which side vessel 52 is received via a radially running channel 72.

In order to make a branch the internal body 60 is pierced through the prosthesis wall from inside, wherein both suturing members moreover penetrate straight through the vessel wall and are pressed into the external body. The barbed hooks on the ends of the suturing members herein ensure a strong suturing in the material of external body 70 so that a reliable connection is established. Hollow stem 62 herein penetrates into side vessel 52 and thus makes an open connection between main blood vessel 50 having prosthesis 40 therein on the one side and side vessel 52 on the other. Via this connection a proper blood circulation through the side vessel is ensured, whereby the circulation to the organs supplied thereby can be fully retained. In similar manner possible other side vessels can if desired also be very quickly connected to the prosthesis.

An alternative embodiment of such branch means is shown in FIG. 4B. In this case stem 62 of first body 60 does not taper, but retains the same inner diameter over its entire length to limit the blood flow as little as possible. A separate mandrel 65 is used to force a perforation in prosthesis wall 40 for stem 62. In preference the body 60 is herein already situated on the mandrel, which is removed afterward. This embodiment of the branch means is further the same as that in FIG. 4A, i.e. the fixation is here also brought about by an anchoring in external body 70.

The embodiment of the branch means shown in FIG. 4D provides fixation in a different way. In this case the stem 62 of internal body 60 comprises at least on its outer end a number of separate fingers which allow a radial movement. On one end thereof are situated one or more suturing members, in this case in the form of barbed hooks 66, which are able to penetrate the vessel wall of the side vessel. For instance using mandrel 65 said fingers are driven apart after the body is positioned. If desired, mandrel 65 can be specifically designed for this purpose, for instance with a local, gradual thickening which drives the fingers apart as mandrel 65 is pulled out of stem 62. An anchoring can thus be realized in side vessel 52, which renders unnecessary a further anchoring in main vessel 50 as in the embodiments of FIGS. 4A and 4B. A significant advantage here is that the vessel wall does not have to be fully perforated and that an in principle foreign external body 70 such as used in the other embodiments can be omitted.

A second embodiment of the suturing means and vascular prosthesis according to the invention is shown in FIGS. 5A and 5B. In this embodiment vascular prosthesis 40 is already provided on the end which has to be connected to the blood vessel with an internal annular body 10 with suturing members 12 forming part of the suturing means. Other than in the first embodiment of the suturing means, the internal annular body here lies on an outer wall of vascular prosthesis 40 and suturing members 12 here penetrate only partially into the vessel wall instead of right through it into an external annular body. In this embodiment annular body 10 has for this purpose an inner diameter which is practically equal to an external diameter of vascular prosthesis 40 and is fixed thereon via a glue connection.

The suturing members are formed by a regular pattern of crater-like openings 14 in the wall of internal body 10, the relatively sharp walls 15 of which form protrusions which are capable of entering the vessel wall under the influence of a radially outward directed force action to thus anchor in the vessel wall the body with the vascular prosthesis fixed thereon. The biocompatible materials for the diverse components are here also carefully chosen, wherein for the internal body high-grade steel is used in which openings 14 are punched. The punched edge unavoidably occurring herein forms the wall 15 of the thus obtained crater-like shape of opening 14.

Figure 6A:
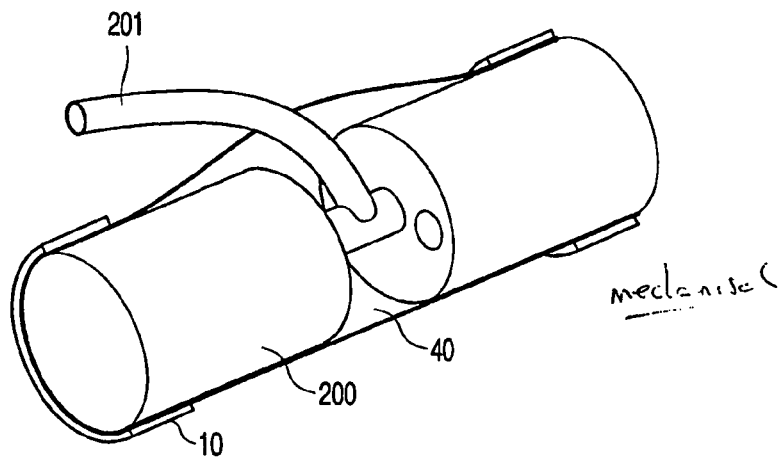
FIGS. 6A-6B show a perspective view of a second embodiment of a device according to the invention.
Figure 6B:
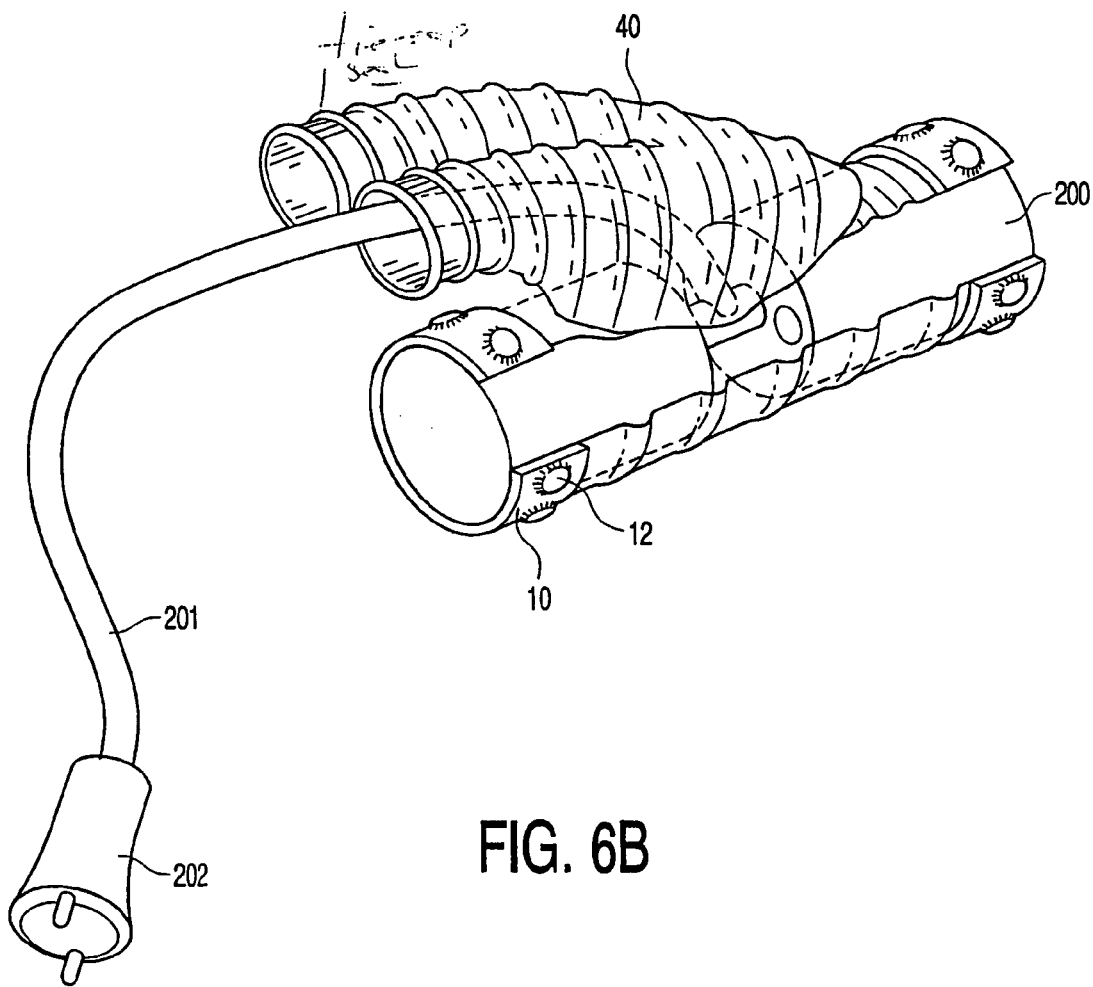

To facilitate insertion of vascular prosthesis 40 with ring 10 thereon, a relatively thin wall thickness is used here, whereby ring 10 is deformable and can be crimped to about 60% of its original diameter, see FIG. 5B. The flexible vascular prosthesis co-deforms herein. In this situation the whole unit is inserted and expanded at the intended location using for instance a second embodiment of a device according to the invention. This device is shown in FIGS. 6A and 6B and comprises an expandable fixation member in the form of an inflatable balloon 200 which in evacuated state can be received in crimped ring 10 and vascular prosthesis 40. In this situation the whole unit is inserted into the blood vessel for treating via an incision arranged for this purpose in the vessel wall. Once prosthesis 40 is situated at the correct location a suitable medium, either a gas or a liquid, is admitted into balloon 200 via a thin flexible infeed line 201, so that it expands together with the vascular prosthesis 40 and ring 10 lying thereon. For this purpose the infeed line 201 is provided on one end with coupling means 202, see FIG. 6B, wherewith a connection can be made in simple manner to means for supplying the medium under pressure.

Admitting of the medium is continued until ring 10 has assumed at least its original shape and protrudes with craters 12 into vessel wall 50. Balloon 200 now has a cylindrical shape with an outer diameter which at least practically corresponds with the internal diameter of the vascular prosthesis 40. Because a balloon wall is used here which is at least practically non-stretch, the vessel wall is prevented from being loaded too much should too much air accidentally be admitted. In practice a pressure in the order of several tens of atmospheres prevails in balloon 200, whereby the balloon behaves as a rigid, non-compressible body which gives sufficient counterpressure to arrange an external annular body round the blood vessel in the above stated manner so that a reliable, leakage proof connection is created between prosthesis 40 and the blood vessel. The medium is then released from balloon 200 again so that it crimps and can be removed easily, whereafter the incision can be closed and the normal blood flow restarted. The patient is now ready for usual aftercare.

Further embodiments of a vascular prosthesis according to the invention are shown in FIGS. 7 to 12. These embodiments form together with the above described embodiments modules of a more extensive embodiment of a vascular prosthesis system according to the invention.

Figure 7:
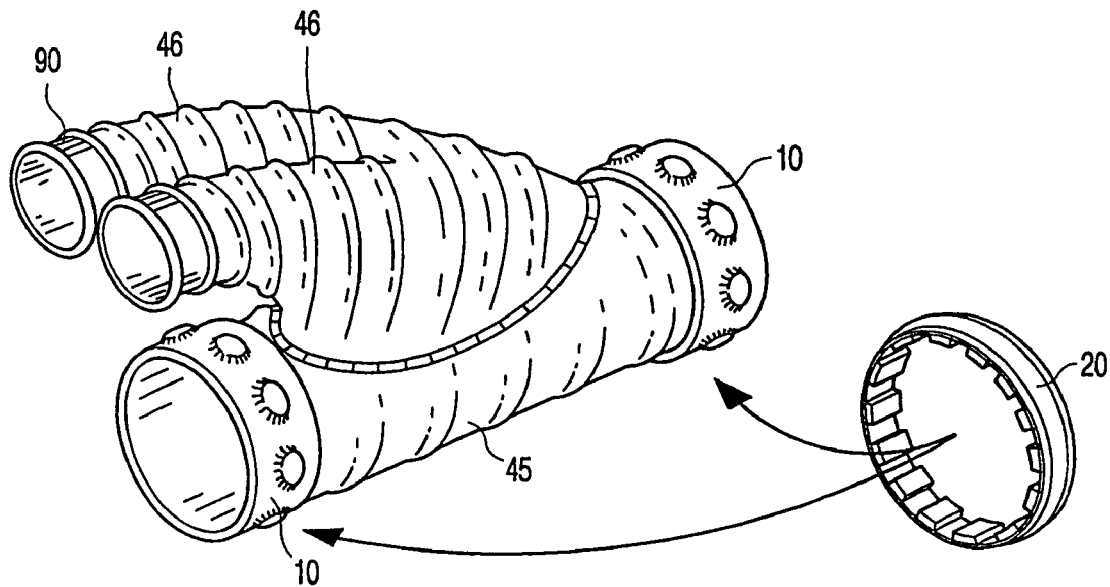
FIG. 7 is a perspective view of a further embodiment of a vascular prosthesis according to the invention which forms a vascular prosthesis module forming part of an embodiment of a vascular prosthesis system according to the invention.

The vascular prosthesis of FIG. 7 was also shown in FIG. 6B and comprises a flexible tubular body with a main leg 45 between the free ends of which at least one and in this case two side legs 46 extend. The free ends of the main leg are herein provided with an internal annular body 10 forming part of the suturing means of the type of FIGS. 5A and 5B which lies on an outer wall of the prosthesis. Both side legs are provided on their ends with coupling means 90, 91 which are capable of an at least practically liquid-tight rapid coupling to a free end of a second flexible tubular body 80 of a second vascular prosthesis.

The coupling means are shown in cross-section in more detail in FIGS. 8A and 8B and comprise per side leg 46 a cylindrical coupling element 90 which is firmly connected by means of a suitable glue connection to the relevant side leg. On a free end the coupling element 90 comprises a slightly conically tapering taper 91 for receiving thereon the free end of the second vascular prosthesis 80. The coupling element here has an internal diameter practically equal to that of vascular prostheses 40,80 so that the blood flow thereof encounters hardly any obstacle.

A mutual connection of both prostheses can be effected simply, rapidly and reliably by sliding the free end of the second vascular prosthesis 80 over taper 91 such that it is clamped fast. Thus achieved is the coupling of FIG. 8B which has already been found extremely reliable in practice. However, in order to further ensure the connection a crimp ring can optionally be placed round the end of the second vascular prosthesis 80 at the position of taper 91 and can be crimped thereon at increased temperature. The shear resistance of the second vascular prosthesis can be further increased by also providing the taper with one or more tangentially running ribs or an otherwise wrinkled or rough surface. In all cases the advantage of a liquid-tight rapid coupling between the two vascular prostheses 40,80 is retained.

The modular embodiment of the vascular prosthesis shown in FIG. 7 is extremely suitable for a double end-to-end anastomosis wherein an incision is made in a main blood vessel for introducing therein of the main leg 45 of the prosthesis. Main leg 45 is subsequently sutured in the main blood vessel as described with reference to FIGS. 6A and 6B, and clamped by means of two external annular bodies 20. Side legs 46 can then each be coupled to an end of a further blood vessel. For this purpose use is made of intermediate prostheses, for instance of the type shown in FIG. 9. These prostheses each comprise a free end and an internal annular body 10 on the other end for suturing to a blood vessel end and form a further module of the prosthesis system. Once both intermediate prostheses, after optionally being shortened to a desired length, are connected to the blood vessel end, the free end is pushed over coupling element 70 to thus complete a double end-to-side anastomosis. The prosthesis of FIG. 9 can otherwise also be deployed per se for a simple end-to-end anastomosis wherein the one end is connected to a first blood vessel end and the free end, with or without interposing of a comparable prosthesis provided with coupling means, is coupled to a second end of the blood vessel. In a variation of this prosthesis (module), the free end is provided with coupling means, which enables a linear extension of free-ending vascular prostheses.

Figure 10:
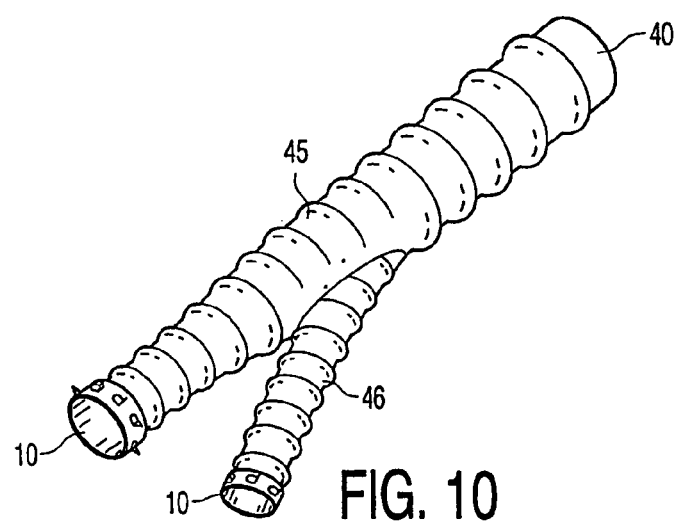

For a multiple end-to-end anastomosis use can advantageously be made of the vascular prosthesis according to the invention shown in FIG. 10 which forms a further module in the prosthesis system. This prosthesis comprises a main leg 45 having on one side a free end which can be coupled to coupling means of another module and on the other side an internal annular body 10 forming part of the suturing means according to an embodiment of the invention. Connected to the main leg between both ends is a side leg 46 which likewise carries such an internal annular body 10 on its end. By means of these bodies 10 the prosthesis can be sutured to respective ends of a first and second blood vessel, while the free end provides the option of either direct suturing to a second end of the first blood vessel or coupling to an intermediate prosthesis which is sutured to this second end and provided on a free end with coupling means according to the invention.

Figure 11:
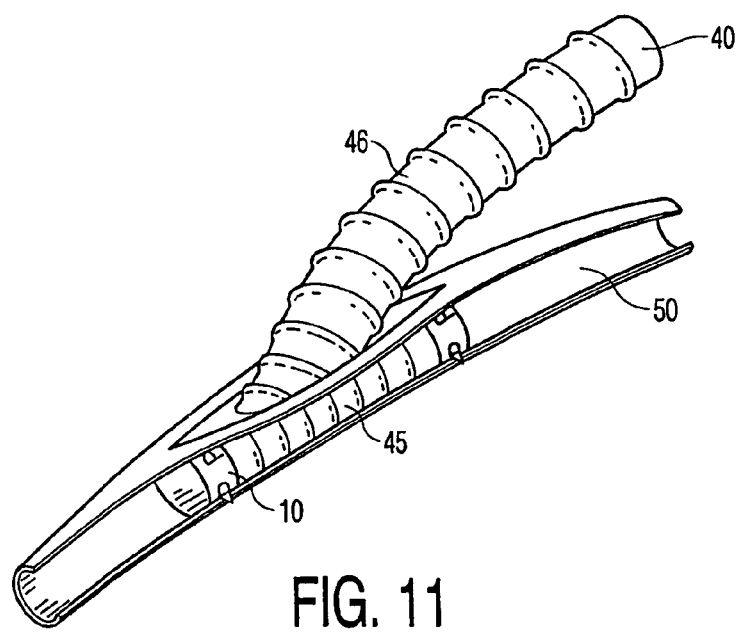

A single end-to-side anastomosis in a blood vessel 50 is shown in FIG. 11. Use is made for this purpose of a further embodiment of the vascular prosthesis according to the invention which forms a corresponding further module in the prosthesis system. This prosthesis is sutured in and on a blood vessel in similar manner to the prosthesis of FIG. 7 and herein provides a single side leg 46 between both ends of the main leg 45 received in blood vessel 50. The free end of side leg 46 can for instance be coupled with the above stated variation of the prosthesis of FIG. 9 to an end of a further blood vessel.

Figure 12:
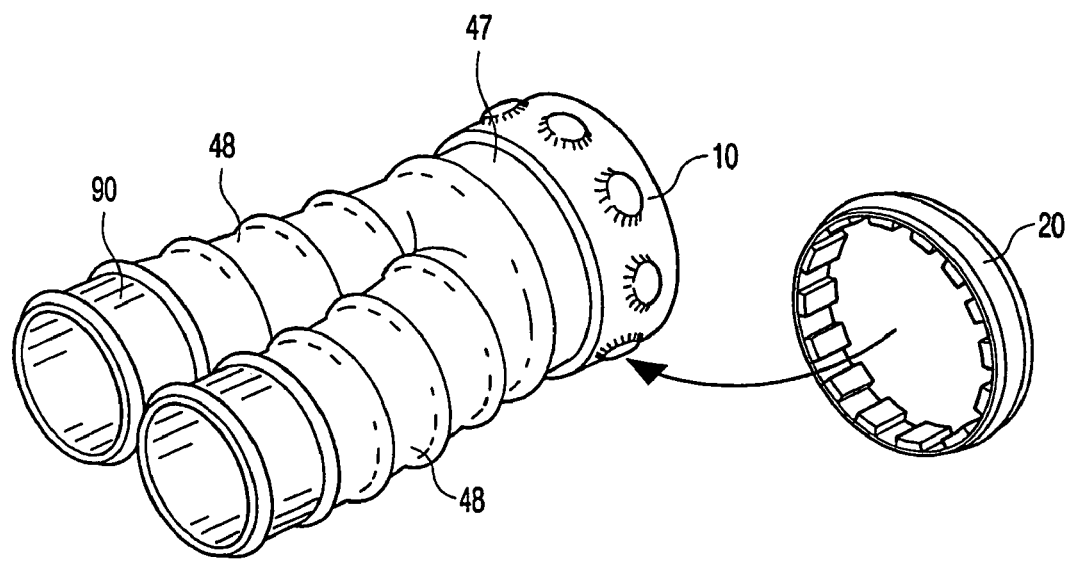
FIGS. 9-12 show a perspective view of further embodiments of a vascular prosthesis according to the invention which each form a vascular prosthesis module forming part of the embodiment of the vascular prosthesis system according to the invention.
Figure 9:
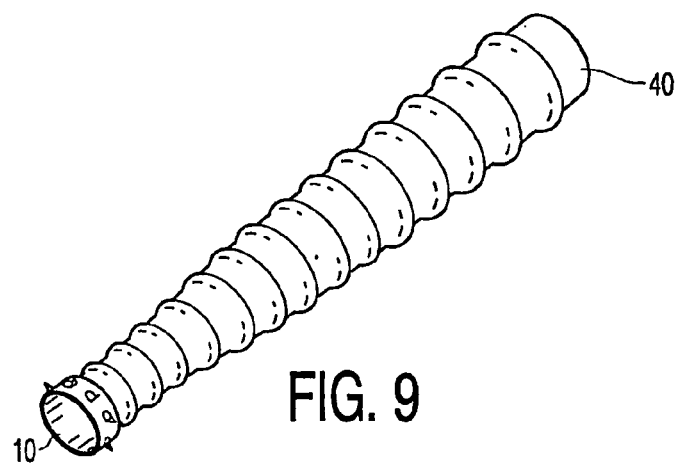

For support or even complete by-pass of a bifurcation use can advantageously be made of the vascular prosthesis according to the invention shown in FIG. 12 which thereby forms a further module within the prosthesis system according to the invention. This vascular prosthesis comprises a tubular body with a primary leg 47 which divides at one end into two secondary legs 48. Making use of this module an aorta-bifemoral bypass can be performed in relatively simple manner. Primary leg 47 of the prosthesis is herein sutured with suturing means 10 to the aorta abdominalis. From the two secondary legs 48 an end-to-end respectively end-to-side anastomosis to the arteria femoralis can then be made with interposing of two prostheses of the type shown either in FIG. 9 or in FIG. 11. If desired, these second prostheses can herein each be individually shortened to a desired length and coupled with the above described rapid coupling to the first vascular prosthesis. Such a prosthesis can also be deployed very practically for a bypass at a higher location between the aorta abdominalis and the arteria iliaca communis, as it can in the case of any other bifurcation.

Although the invention has been further described above solely with reference to a single embodiment, it will be apparent to all that the invention is in no way limited to the given examples. On the contrary, many variations and embodiments are possible for the average skilled person within the scope of the invention. The vascular prosthesis system can thus be extended with additional prosthesis modules, each for a specific operation or for a similar type of surgery but with other dimensions and/or couplings.

Many variations of the shown suturing means are also possible for an average skilled person without having to depart from the scope of the invention. Different types of suturing member can thus be applied and the internal and external annular bodies can also be manufactured from other materials and can be designed or embodied differently. More particularly the annular bodies can for instance be provided with perforations to enhance the acceptance and accommodation thereof in the body. For insertion and clamping of the prosthesis according to the invention alternative devices can also be used instead of the described device and balloon, for instance a device with outward scissoring parts which can be forced apart from a distance.

The invention generally provides a completely new surgical procedure in respect of the processing of vascular prostheses which draws much less heavily on the condition of the patient than the more conventional surgery.

The invention claimed is:

1. A vascular prosthesis provided with branch means, for connecting a branch vessel to a vascular prosthesis arranged in a main blood vessel, said vascular prosthesis comprising a hollow tubular member, and said branch means comprising:
   a internal body inside said tubular member having a flange-shaped portion adjacent an inner wall of said tubular member and comprising a rigid hollow stem and at least one rigid barb member, said stem and said at least one barb member protruding from said flange-shaped portion and penetrating through said wall of said tubular body, in which said stem comprises a hollow channel opening at a free distal side of said stem external of said wall of said tubular member and opening at a proximal side of said stem inside said tubular body; and
   a disc-shaped external body registering with said flange-shaped portion at a side of said wall of said tubular member opposite said flange-shaped portion of said internal body, said disc-shaped external body having a bore, said stem extending through said bore, and having a circumferentially extending body portion which receives a free end of said at least one barb member to engage into a firm mutual connection with said internal body,
   wherein, during use, a wall of said main vessel and said wall of said tubular member are jointly clamped between said flange shaped portion of said internal body and said circumferentially extending body portion of said external body, and
   wherein, during use, said stem extends inside said branch vessel thereby creating an open fluid connection between said main vessel and said branch vessel through said channel.

2. The vascular prosthesis as claimed in claim 1, wherein said stem tapers down at a free distal end into a sharp pointed end portion.

3. The vascular prosthesis as claimed in claim 1, wherein said disc-shaped external body comprises a channel between a peripheral edge of said body portion and said bore to provide access to said bore from said peripheral edge.

4. The vascular prosthesis as claimed in claim 1, wherein said internal body is made of metal and said external body is made of a plastic.

* * * * *